US009551692B2

(12) United States Patent
Gottfried (10) Patent No.: US 9,551,692 B2
(45) Date of Patent: Jan. 24, 2017

(54) METHOD FOR ESTIMATING DETONATION PERFORMANCE OF MATERIALS

(71) Applicant: U.S. Army Research Laboratory ATTN: RDRL-LOC-I, Adelphi, MD (US)

(72) Inventor: Jennifer L. Gottfried, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 198 days.

(21) Appl. No.: 14/496,115

(22) Filed: Sep. 25, 2014

(65) Prior Publication Data
US 2016/0091464 A1     Mar. 31, 2016

(51) Int. Cl.
*G01N 29/24*     (2006.01)
*G01N 29/024*    (2006.01)
*G01N 29/44*     (2006.01)

(52) U.S. Cl.
CPC ........ *G01N 29/2418* (2013.01); *G01N 29/024* (2013.01); *G01N 29/4445* (2013.01); *G01N 29/4472* (2013.01); *G01N 2291/011* (2013.01)

(58) Field of Classification Search
CPC ............ G01N 29/2418; G01N 29/4472; G01N 29/4445; G01N 29/024; G01N 33/227
USPC ................................ 73/31.01, 31.05, 31.07, 35.14–35.17, 73/865.6, 866
See application file for complete search history.

(56) References Cited

U.S. PATENT DOCUMENTS

| 4,336,085 | A  | * | 6/1982  | Walker ............... C06B 23/005 149/100 |
| 5,131,957 | A  | * | 7/1992  | Epstein ............. B23K 26/0069 148/513 |
| 5,386,778 | A  | * | 2/1995  | Sullivan, Jr. ............ F42B 35/00 102/302 |
| 6,438,191 | B1 | * | 8/2002  | Bickes, Jr. ............... F42D 3/00 102/302 |
| 7,669,460 | B1 |   | 3/2010  | Sandusky et al. |
| 8,082,844 | B1 | * | 12/2011 | Barker ................ F42B 12/207 102/200 |

(Continued)

OTHER PUBLICATIONS

Jennifer L. Gottfried, "Influence of exothermic chemical reactions on laser-induced shock waves," Phys. Chem. Chem. Phys. 2014, 16, 21452-21466. (First published online Sep. 3, 2014).

(Continued)

*Primary Examiner* — Helen Kwok
(74) *Attorney, Agent, or Firm* — Eric Brett Compton (57) ABSTRACT

A method for estimating the detonation performance of a material is executed by first preparing a small sample of the material to be tested. That sample is lased with a laser beam having sufficient energy to induce a plasma from a portion of the sample and to produce a shock wave, without detonation of the sample. The velocity of the shock wave is then measured at different times. And a characteristic shock velocity determined for the material based on the relationship between shock velocity and time. The characteristic shock velocity represents the velocity of the shock wave at the point in time when the shock front expands freely without additional energy input from the plasma or subsequent chemical reactions. The characteristic shock velocity can be used to determine whether a material is non-energetic or energetic; if it is energetic, the estimated detonation performance can be determined.

20 Claims, 7 Drawing Sheets

(56) References Cited

U.S. PATENT DOCUMENTS

| | | | | |
|---|---|---|---|---|
| 2009/0105738 A1* | 4/2009 | Apperson | ........ | A61B 17/22004 606/167 |
| 2010/0180786 A1* | 7/2010 | Goodridge | .............. | F42D 1/043 102/201 |
| 2011/0210479 A1* | 9/2011 | Yang | .................... | B23K 26/063 264/400 |
| 2013/0262005 A1* | 10/2013 | Lundgren | ............... | G06F 17/11 702/64 |
| 2015/0241191 A1* | 8/2015 | Garcia | .................... | F42D 1/042 102/311 |
| 2015/0268216 A1* | 9/2015 | Chavez | ................ | G01N 33/227 436/156 |

OTHER PUBLICATIONS

Jennifer L. Gottfried, "Laser-induced shock chemistry of energetic materials," proceeding paper and slide presentation presented at the 15th International Detonation Symposium, Jul. 17, 2014.

Jennifer L. Gottfried, "New laboratory-scale method for the determination of explosive performance from laser-induced shock waves," poster display at the Gordon Research Conference on Energetic Materials, Newry, MR (Jun. 15-20, 2014).

Jennifer L. Gottfried, "New Laboratory-Scale Method for the Determination of Explosive Performance from Laser-Induced Shock Waves," proceeding paper and slide presentation presented at the 61st JANNAF Propulsion Meeting/38th PEDCS, May 22, 2014.

Jennifer L. Gottfried, "New Laboratory-Scale Method for the Determination of Explosive Performance from Laser-Induced Shock Waves," ARL-TR-6844, Army Research Laboratory, Mar. 2014.

Sukesh Roy et al., "Spatially and temporally resolved temperature and shock-speed measurements behind a laser-induced blast wave of energetic nanoparticles," Journal of Applied Physics, 113, 184310 (2013).

N. K. Bourne, "On the laser ignition and initiation of explosives," Proc. R. Soc. Lond. A (2001) 457, 1401-1426.

Yeshayahu Ben-Eliahu and Yehuda Haas, "Laser Initiation of the Decomposition of Energetic Polymers: Shock Wave Formation," J. Phys. Chem. 1995, 99, 6010-6018.

Modesto J. Barbarisi and Edward G. Kessler, "Initiation of Secondary Explosives by Means of Laser Radiation," Technical Report 3861, Picatinny Arsenal, Dover, NJ, May 1969.

* cited by examiner

ND FOR ESTIMATING DETONATION
METHOD FOR ESTIMATING DETONATION PERFORMANCE OF MATERIALS

GOVERNMENT INTEREST

The invention described herein may be manufactured, used, and licensed by or for the United States Government.

BACKGROUND OF THE INVENTION

I. Field of the Invention

The present invention relates to a method for estimating the detonation performance of materials.

II. Description of Related Art

The detonation performance of energetic or explosive materials constitutes an important factor in many military applications as well as civil applications. The detonation performance includes the energy of detonation, the detonation pressure, and detonation velocity.

In order to determine the detonation performance of newly developed energetic materials, it has previously been necessary to amass enough of the energetic material to form a sample capable of detonation. That sample was then detonated and the various factors for detonation performance measured during the detonation.

The previously known methods for determining the detonation performance of an energetic material, however, suffer from several disadvantages. First, in many cases a newly developed energetic material is only available in small quantities, such as milligrams. As such, there is simply insufficient material to create the detonation. In these cases, it was not possible to accurately estimate the detonation performance of the energetic material until a sample sufficiently large for detonation was collected. However, in some cases the energetic material did not exhibit sufficient detonation performance so that the time and cost expended to create a sample of sufficient mass for detonation was wasted.

A still further disadvantage of the previously known methods for determining the detonation performance of an energetic material is that the actual detonation of the energetic material must necessarily be carried out in a safe test area outside the laboratory. This, in turn, disadvantageously increased the time and cost to test the energetic material due to the large number of personnel required to perform the testing and the necessary safety precautions.

SUMMARY OF THE PRESENT INVENTION

The present invention provides an innovative methodology for estimating the detonation performance of a material which overcomes the above-mentioned disadvantages of the previously known methods.

A sample of the material is first prepared. However, unlike the previously known methods which detonate the sample, the sample may have a mass of only a few milligrams (e.g., 10-20 mg) and still be sufficient to carry out the methodology. In some implementations, the sample material is applied to one side of a double-sided tape having its other side affixed to a glass slide.

The sample is then subjected to a laser beam of sufficient energy to induce a plasma from a portion of the sample and to produce a laser-induced shock wave, without detonation of the sample. A laser beam having an energy of about 900 millijoules/pulse, a wavelength of about 1064 nanometers, and a pulse duration of about 6 nanoseconds, for instance, may be focused onto the sample. The laser-induced shock wave is similar to a detonation wave and the velocity of the laser-induced shock wave correlates to the detonation performance of the sample material. A high-speed camera may be used, for example, to record the shock wave moment as a plurality images from a single laser shot.

Consequently, the velocity of the shock wave is measured at different times using successive images recorded by the high-speed camera. A linear scale with known dimensions may be included as a part of the recorded shock wave in some implementations for this purpose.

Once the velocity of the shock wave has been measured, a characteristic shock velocity for the material is determined based on the relationship between shock velocity and time. The characteristic shock velocity represents the velocity of the shock wave at the point in time when the shock front expands freely without additional energy input from the plasma or subsequent chemical reactions. For example, a best fit function, such as a 5th order polynomial, may be applied to fit multiple velocity measurements as a function of time, and the characteristic shock velocity is determined by finding the y-intercept of the best fit function.

The characteristic shock velocity provides important information regarding the detonation performance of the material. For instance, it enables the material to be classified as being energetic or non-energetic, and the detonation performance of the material to be estimated, e.g., by comparing the characteristic shock velocity with theoretically predicted or empirical data from detonation of energetic material(s).

The methodology for estimating detonation performance of a material may be implemented by an innovative apparatus in various embodiments. The apparatus may include a stage for holding a sample of the material; a laser configured to output a laser beam having sufficient energy to ablate the sample and form a plasma from a portion of the sample and to produce a shock wave, without detonation of the sample; a high-speed camera configured to record the shock wave movement in a plurality of sequential image frames; and a controller. The controller can be configured to: measure the velocity of the shock wave at different times; and determine a characteristic shock velocity for the material based on the relationship between shock velocity and time.

The apparatus may include a schlieren imaging apparatus having: a pair of spaced-apart mirrors placed on opposing sides of the sample stage; an illumination source for focusing light onto a first of the pair of mirrors, through a sample laser-ablation area in the vicinity of the sample stage where the shock wave passes, and onto a second of the pair of mirrors; and an knife edge placed at the focal spot of the second of the pair of mirrors to limit light rays to the high-speed camera. The high-speed camera photographs light and dark striations representing differences in the refractive index of air in the sample laser-ablation area. Additionally, the apparatus may further include an electronic database configured to store characteristic shock velocity values for materials.

Unlike the previously known methods for determining the detonation performance of the sample, since the method of the present invention requires only a small sample, the method of the present invention may be carried out safely in laboratory conditions.

BRIEF DESCRIPTION OF THE DRAWING

The present invention will be described in greater detail with reference to the drawings in which.

DETAILED DESCRIPTION OF EMBODIMENTS OF THE PRESENT INVENTION

An innovative methodology for estimating detonation performance of materials will now be described. In brief, this methodology images a shock wave generated by the formation of a laser-induced plasma on the surface of a material of interest, without detonating the material. This laser-induced shock wave is similar to a detonation wave and the velocity of the laser-induced shock wave correlates to the detonation performance of the sample material. The shock wave's velocity is measured at different times to determine a characteristic shock velocity of the material which represents the velocity of the shock wave at the point in time when the shock front expands freely without additional energy input from the plasma or subsequent chemical reactions. Additionally, the detonation performance for the sample material can be estimated based on the determined characteristic shock velocity. For example, the determined characteristic shock velocity can be correlated with theoretically predicted or empirical data from the large-scale detonation of energetic material(s).

Army Research Laboratory Technical Report ARL-TR-6844 titled "New Laboratory-Scale Method for the Determination of Explosive Performance From Laser-Induced Shock Waves" published in March 2014 is hereby incorporated by reference in its entirety. This report provides more specific details on some initial experiments and experimental data conducted by the inventor validating this methodology, and demonstrates the utility of a methodology for the estimation of detonation performance of materials. Results of those experiments show that laser-induced decomposition of materials under the specified experimental conditions generates a blast wave which is similar to actual detonation waves. One major difference is that the shock front travels first through the plasma plume containing evaporated material and then through the ambient air, as opposed to a true detonation wave that travels through the solid energetic material.

Figure 1:
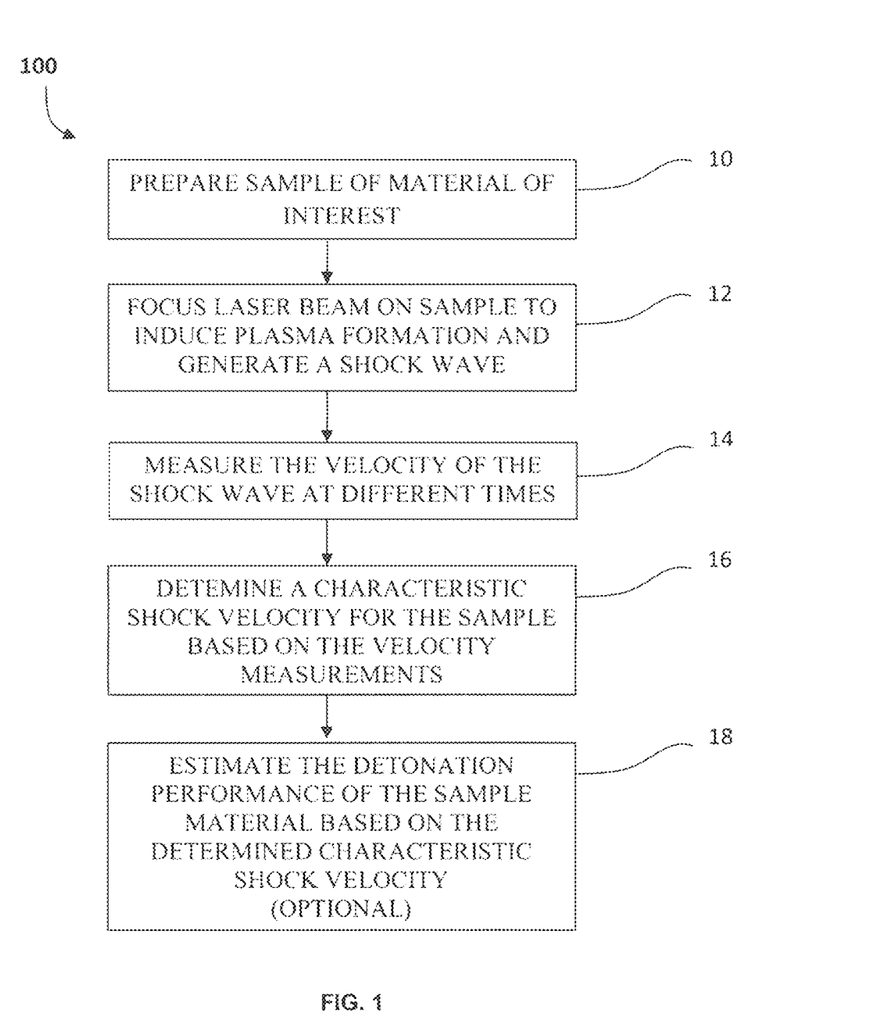
FIG. 1 is a flowchart of the methodology of the present invention for estimating detonation performance of a material.

FIG. 1 is a flowchart of the methodology 100 of the present invention for estimating detonation performance of a material. With reference to FIG. 1, in order to estimate the detonation performance of a material in accordance with the present invention, a sample of the material is first prepared at step 10.

In theory, any type of material can be sampled since a laser-induced plasma (and subsequent shock wave) can be generated from all materials with sufficient laser energy. Materials can generally be classified as either being energetic or non-energetic. Energetic materials are characterized as having a high amount of stored chemical energy that can be released. A sub-class of energetic materials is explosive materials.

Energetic materials may include, for example, black powder, smokeless gun powder, 1,3-dinitrobenzene, 1,4-dinitrobenzene, DNAN, HNS, TNT, RDX (Class 1 and Class 5), HMX, PETN, TATB, NTO, CL-20, composition-A3, composition-B, and pentolite. Non-energetic materials, such as the blank (double-sided tape on a glass slide), graphite lubricant (micron-size), diamond (25-35 µm), nanographite (1-4 µm wide, 50 nm thick), graphite nanoparticles (3-4 nm), sugar, melamine, L-glutamine, Epsom salt, and ammonium nitrate were also collected for comparison.

Unlike the previously known methods which detonate material, however, only a few milligrams, e.g. 10-20 mg, of the material in solid form, such as powder, are needed to perform the methodology of the present invention. In some embodiments, the sample is applied to one side of a double-sided tape having its other side affixed to a glass slide. The important quantity is the amount of material that is ablated by the laser. This depends on many different parameters and is difficult to quantify (e.g., much of the material is blown off the slide by the shock wave). If the samples are consistently prepared as described (pressed firmly into tape, with fixed laser energy and spot size, etc.), the quantity of material on the sample slide is not critical. After the sample has been prepared, step 10 proceeds to step 12.

Figure 2:
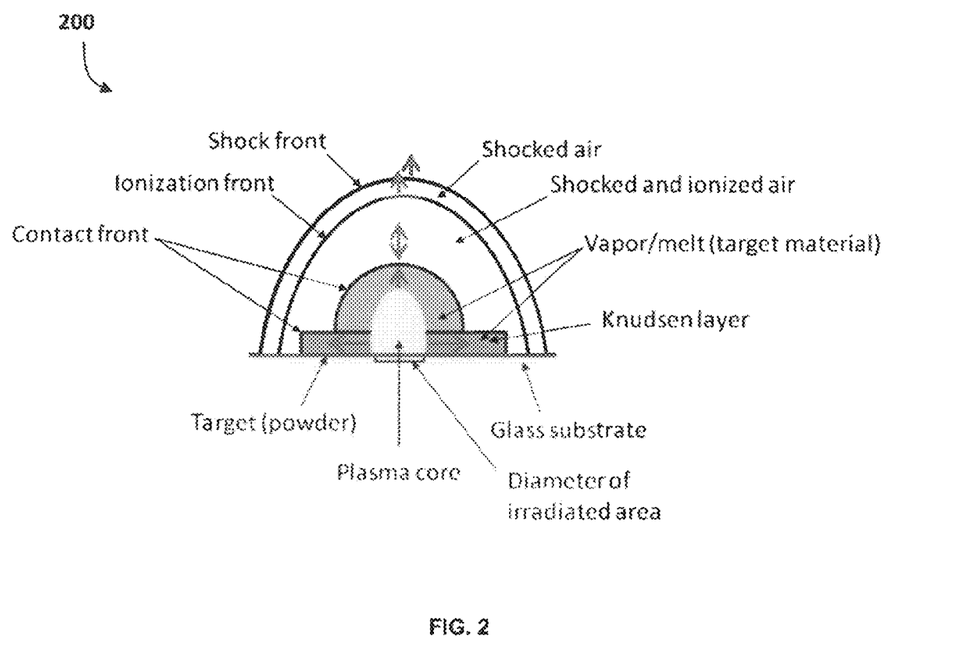
FIG. 2 shows a plasma and shock structure.

At step 12 the sample is lased with a laser having sufficient energy to form a plasma from an ablated portion of the sample, producing a shock wave. In general, at high laser irradiances (typically higher than $10^7$ W/cm$^2$), a shock front analogous to a detonation can be produced from nearly any material. The interaction of the laser beam with the plasma results in compression of the vaporized gas by the absorption of the laser energy, contributing to the heating and ionization of the ablated material. The velocity in this region is supersonic with respect to the ambient gas, and a laser-supported detonation wave is produced. The laser-supported detonation wave is present only during the laser pulse (e.g., up to about 6 ns during the laser pulse), but it helps initiate the chemical reactions that contribute to the blast wave expansion which is the main shock front that is directly measured for this method. This main shock front is shown in FIG. 2. It is noted that at irradiances lower than about $10^6$ W/cm$^2$, laser-supported combustion occurs and the laser energy is absorbed in the plasma behind the shock wave with no contribution to the thrust from the blast wave expansion.

In one exemplary setup, a laser is utilized to ablate the sample at step 12. The output from the laser may be focused through a lens system to concentrate the laser output in a sufficiently small area to ablate the sample, or a portion of the sample, into a plasma state. In practice, an Nd:YAG laser having a near-infrared wavelength of 1064 nanometers, a pulse duration of 6 nanoseconds, and an energy output of 900 millijoules/pulse may be used to lase the sample, although other pulsed lasers may alternatively be used. The spot area for each laser pulse preferably is about $5.0 \times 10^{-3}$ cm$^2$ with a fluence of about 180 joules/cm$^2$ and a peak power density or irradiance of about $3.0 \times 10^{10}$ watts/cm$^2$.

Upon ablation of the sample, a plasma and shock structure 200 is shown in FIG. 2 is created. Both the laser-induced plasma generated from a thin residue of material applied to tape on a glass substrate and the shock structure of the resulting blast wave are shown in the figure. The arrows indicate the direction of propagation for the plasma and various fronts. The presence of the contact fronts, ionization front, and shock front has been confirmed through shadowgraph imaging. The propagation of the blast wave is determined by the amount of energy released into the plasma state. An exhaust inlet should connect to the laser-ablation setup to remove any vapors and particulate matter to avoid accidental inhalation. Typically the laser is normal to the sample surface, and the hemi-spherical blast wave propagation expands into the surrounding air above the sample surface.

Following ablation of a portion of the sample and the resulting laser-induced plasma, the plasma begins to cool. During the cooling process, recombination reactions of the ablated material produce molecular species including combustion gases. When the chemical reactions in the plasma are exothermic, the plasma temperature is increased, thus increasing the velocity of the resulting shock wave which expands outwardly away from the sample. The velocity of that shock wave correlates to the detonation performance of the material forming the sample. Typical shock wave velocities near the laser-material interaction region are tens of kilometers per second, corresponding to pressures of tens or hundreds of gigapascals.

Although any means may be used to image the ablation, preferably a schlieren imaging technique may be used to visualize the laser-induced shock wave. Schlieren imaging is a known process that is used to visualize the flow of fluids of varying densities. The camera frames provide a two-dimensional (2-D) image of the fluid (e.g., air) flow above the sample surface.

More particularly, in this innovative methodology 100, the imaging of a shock wave generated from a laser-induced plasma of sample material is of importance. Experiments were initially conducted in air; although other mediums may be used instead. For example, there might be some advantages to expanding the shock wave into other gases (e.g., into argon or helium, which would change the chemical reactions that occur in the laser-induced plasma; this is important if one wants to test the explosive material under anaerobic conditions). There would also be an advantage to expanding the shock wave into a vacuum, since there would be no air resistance to slow it down and additional useful data points could potentially be obtained.

Figure 3:
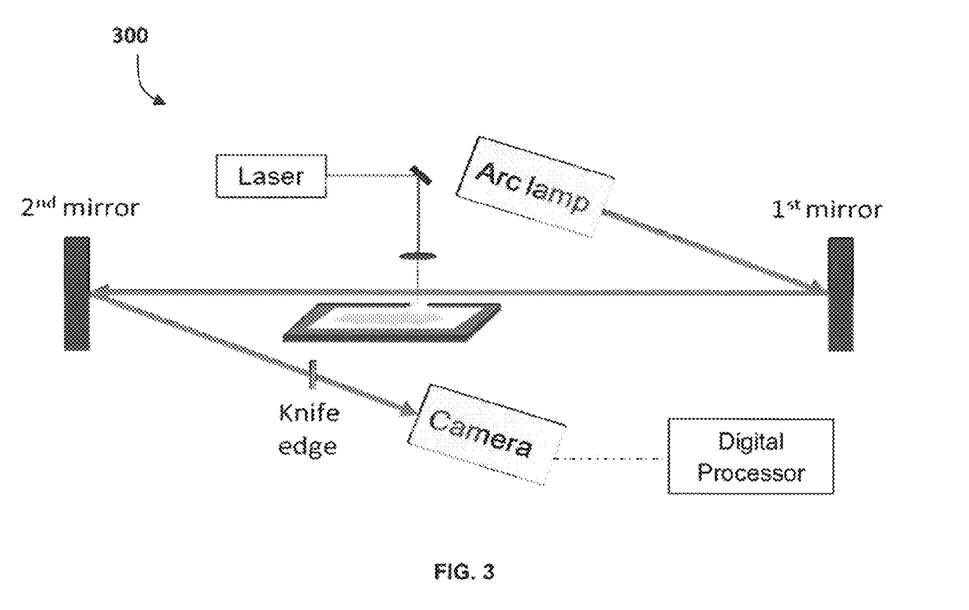
FIG. 3 shows a simplified schematic of an apparatus used to measure the shock wave according to an embodiment.

FIG. 3 shows a simplified schematic of an apparatus 300 used to measure the shock wave according to an embodiment. An arc lamp (Newport Oriel model 66476) with a 200-W Hg—Xe ozone-free lamp (model 6290) serves as the illumination source, which was focused onto the first mirror with an aspheric condenser lens. The light is collimated between the two schlieren mirrors (10.8-cm diameter, 114-cm focal length), spaced 211 cm apart, for example. The sample can be placed on a vertical stage in the test section between the two mirrors, and the ablation laser focused on the sample surface from above. In order to prevent breakdown of the air above the target, the plane of the target surface should be placed generally close to the focal point of the lens of the camera (e.g., 1.5 mm above the focus). Changes in the refractive index of the air caused by the formation of the laser-induced plasma bend the light rays, so that when the light was focused after the second mirror, a knife edge (or graded linear filter) placed at the focal spot can be used to cut out approximately half the light rays; the schlieren images thus correspond to the first spatial derivative of the index of refraction. A high-speed color camera (Photron SA5) can record the light and dark striations in the images representing differences in the refractive index of air in the test region. A zoom lens (Nikon Nikkor 24-85 mm f/2.8-4D IF) on the camera focuses 33 cm in front of the focus of the ablation laser. This focal position is optimized to provide the greatest contrast for visualization of the shock wave. The following camera settings can be used for imaging the shock waves: 84,000 frames per second (fps), 1.0-μs shutter, 64-×648-pixel image size. Other types of detection schemes such as shadowgraphy and high brightness imaging may alternatively be used to measure the velocity of the shock wave.

Figure 4A:
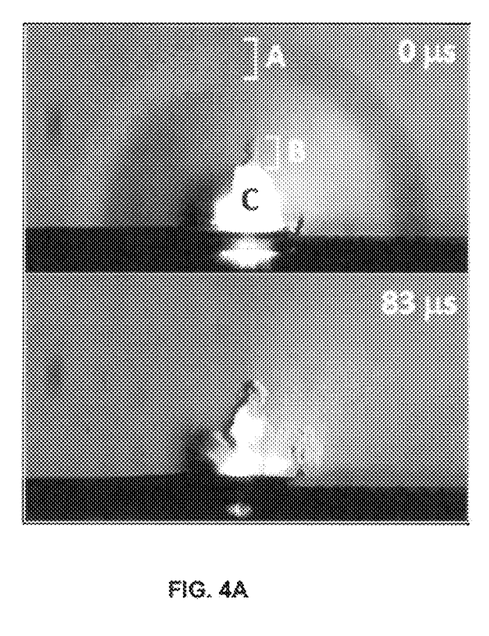
FIGS. 4A and 4B show images from the high-speed video of the laser ablation of sample materials.

FIGS. 4A and 4B show images from the high-speed video of the laser ablation of sample materials. FIG. 4A shows two snapshots from the high-speed video (12,000 fps; 9.8-μs shutter) of the laser-ablated blank tape substrate. In the first frame (upper), the shock wave (A) and plasma plume (C) were observed at a delay time of 0 μs. In addition, a thin column of heated air (B) above the plasma plume was observed. This region is evidence for the presence of a laser-supported detonation wave produced during the laser pulse. As the plasma cools the atomized and excited carbon combusts in the air (at times greater than 83 μs). As the second frame (lower) shows, the density gradient caused by the high-temperature plasma is no longer distinguishable from this region.

Figure 4B:
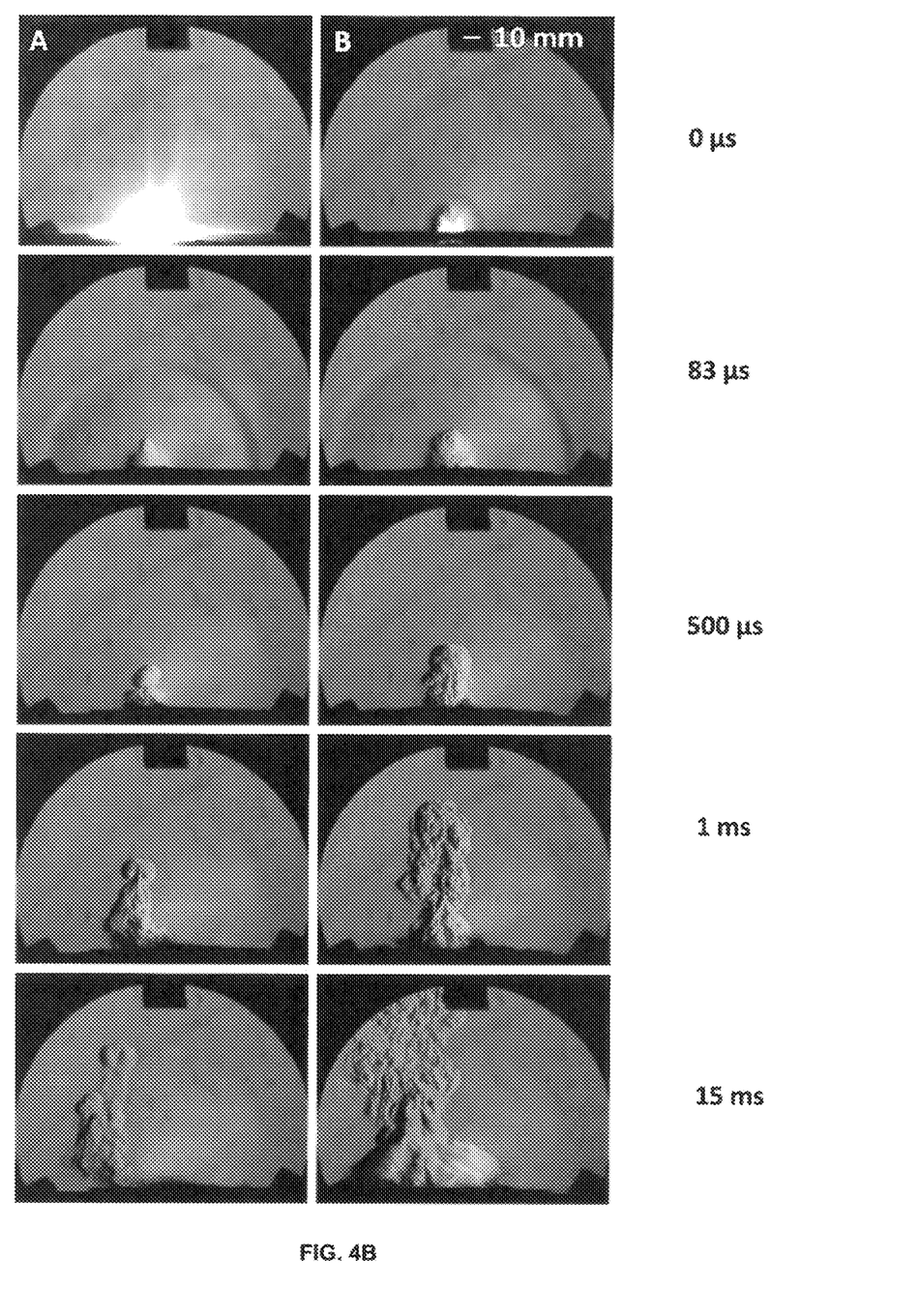

FIG. 4B shows images from the laser ablation of two materials, (A) a non-energetic material (L-glutamine) and (B) an energetic material (RDX). The video was collected using a high-speed camera (12,000 fps; 9.8-μs shutter). The first frame after the laser pulse (0 μs) shows the laser-induced plasma, which is typically more luminescent for non-energetic materials. Because of the decrease in brightness, the laser induced shock wave is visible in the first frame of the RDX video. The second frame (83 μs) shows the roughly hemispherical propagation of the shock wave (which is faster for the RDX). The high-resolution video also shows the ejection of material from the target surface, resulting from the impact of the internal shock wave. By 500 μs, the light emission was gone for both materials, and the heat-affected zone in the background air caused by the plasma formation was clearly visible for both samples; the RDX produces a significantly larger zone. At later times (greater than 1 ms), the pull of the exhaust on the heated air and unreacted particles was observed for the L-glutamine. By 15 ms, RDX particles ejected from the sample surface started deflagrating as they reached the heated air above the sample surface (resulting in additional light emission and rapid vertical and horizontal expansion of the heated area).

The shock wave produced by the laser-induced plasma may be measured and quantified. While there may be multiple shock waves produced by the laser ablation, the main external shock wave is the one that is preferably measured since it is the strongest. Returning to FIG. 1, after the shock wave has been created, step 12 proceeds to step 14 where the velocity of the shock wave is measured at different times. The number of measurements depends on the number of frames obtained from the high-speed camera. Ideally, as many measurements as possible during the first several hundred microseconds are acquired.

In one embodiment, a high-speed camera, i.e. a camera that takes temporally spaced images at a very high rate, e.g. 84,000 frames per second, is used. The measurement of the speed of the shock wave or shock front is determined from the camera image frames. With the high-speed camera, the shock wave from a single ablation event can be observed in multiple frames and its velocity measured.

For example, a linear scale, such as a ruler or other item with known dimensions, can be included as a part of the photographed ablation. Since the frame rate is known, e.g. 84,000 frames per second, the time difference between sequential frames is calculated to be 1/84,000 seconds or about 0.0000119 seconds. The speed of travel of the shock wave is then simply (travel distance between sequential frames/ 0.0000119 seconds). This velocity measurement is an instantaneous measurement at that point in time. Multiple velocity measurements for the sample at various different times can be obtained in this manner to create a velocity vs. time plot.

If a digital video camera is provided (or the video data otherwise converted to digital), a digital processor or controller (FIG. 3) can be configured to automate the velocity measurements in the manner in implementing the methodology. The processor or controller may be implemented as hardware, software or a combination thereof specifically configured to execute coding or instructions necessary to implement embodiments of the present invention. Processor-executable code can be stored in a memory device and execute by the processor or controller as needed. In some implementations, software code (instructions), firmware, or the like, may be stored on a computer or machine-readable storage media. The processor(s) may be a programmable processor, such as, for example, a field-programmable gate array (FGPA) or an application-specific integrated circuit (ASIC) processor. The methodology disclosed herein may be implemented and executed by an application created using any number of programming routines, such as MATLAB. Of course, any number of hardware implementations, programming languages, and operating platforms may be used without departing from the spirit or scope of the invention. As such, the description or recitation of any specific hardware implementation, programming language, and operating platform herein is exemplary only and should not be viewed as limiting.

Figure 5:
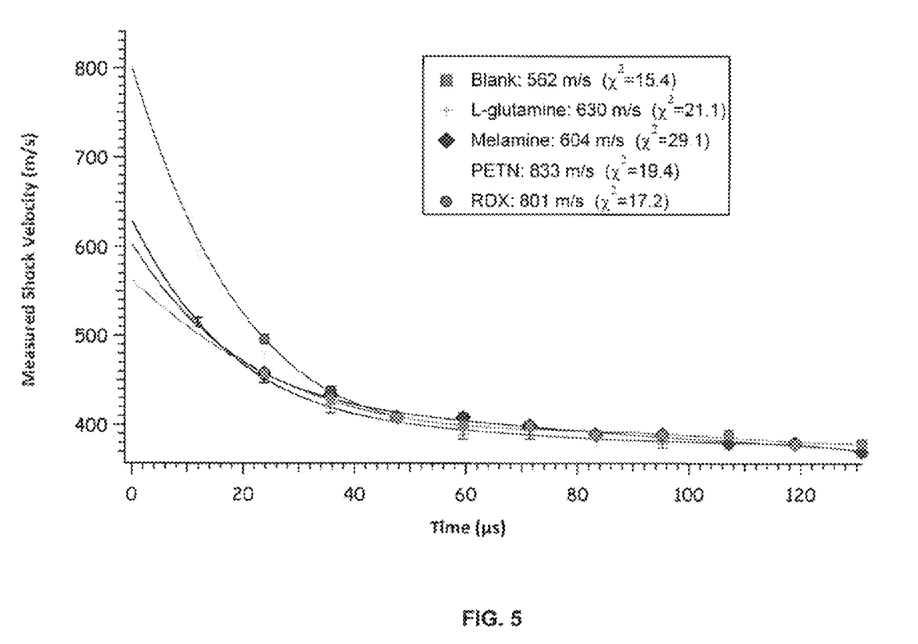
FIG. 5 shows the measured shock velocity values over time for five different sample materials.

FIG. 5 shows the measured shock velocity values over time for five different sample materials. These materials included the blank tape, L-glutamine, melamine, PETN and RDX. The shock velocity values in meters/second were taken at time intervals of about 12 μs. In general, the velocity of the shock wave decreases exponentially with each successive frame ultimately approaching the speed of sound in air at 343 m/s.

Turning back to FIG. 1, once the velocity of the shock wave has been determined for different times for a sample material at step 14, the methodology proceeds to step 16 where the characteristic shock velocity is determined for the material based on the velocity measurements in step 14.

The data (measured shock velocity vs. time) for each sample can be characterized by a best fit function. Fitting functions are well-known and may be implemented by various means, such as MATLAB data fitting functions. Three or more data points can be used to fit the data. Although, it should be appreciated that obtaining even more data points and at earlier times improves the accuracy of determining the characteristic shock velocity. The faster the camera speed the better the ability to provide such measurements.

Given the general nature of the data observed, a 5th order polynomial fitting function may be used, for example, as was used in FIG. 5 for the five sample plots. The value $\chi^2$ represents the statistical 'goodness' of the fitting function, with smaller values of $\chi^2$ indicating a better fit. Although, it will be appreciated that other best fitting techniques or functions could also be used.

The actual velocity of the shock wave at very early times (nanosecond timescale) and is on the order of kilometers per second when it is being accelerated by the supersonic expansion of the plasma plume. The characteristic shock velocity of the material represents the velocity of the shock wave at the point in time when the shock front expands freely without additional energy input from the plasma or subsequent chemical reactions. The y-intercept of the fitting function is defined to be the characteristic shock velocity for the sample material according to the methodology.

The aforementioned digital processor or controller (or a separate one) may also be configured to automate the characteristic shock velocity determination for the sample material in this manner in implementing the methodology.

In order to account for shot-to-shot variations in the laser-material interaction and increase the statistical significance of the data, multiple laser shots (with concomitant measurement of the characteristic shock velocity) should be obtained for each sample of interest. The measured characteristic shock velocities from each laser shot should be averaged together to determine the characteristic shock velocity of the sample. A minimum of 5-10 laser shots per sample is advisable for best accuracy.

The differences in the characteristic shock velocities of the samples are believed to be due to different chemical reactions involved which are unique to a particular material. As shown in FIG. 5, the characteristic shock velocities (from one laser shot) of PETN is about 833 m/s and RDX is about 801 m/s which are significantly higher than those of the inert materials (562-604 m/s).

Steps 10-16 may be repeated for many materials. The characteristic shock velocity values for these materials can be stored in an electronic database or library, for later retrieving and referencing.

Next, the methodology in FIG. 1 optionally proceeds to step 18, where the detonation performance for the sample material can be estimated based on the determined characteristic shock velocity. In this step, the determined characteristic shock velocity can be correlated with previously-stored, theoretically predicted and/or empirical data for the detonation performance of energetic material(s), for example. This correlation step can be useful primarily for two main purposes: 1) to determine and classify whether a sample material is non-energetic or energetic based on the determined characteristic shock velocity, and 2) if it is energetic, the determined characteristic shock velocity can be used to estimate the detonation performance.

With respect to the first purpose, most materials can be broadly classified based on their characteristic shock velocity. For instance, the determined characteristic shock velocity for a material can be analyzed to see if it meets a minimum threshold for measured shock velocity. This can be a simple comparison test.

Figure 6:
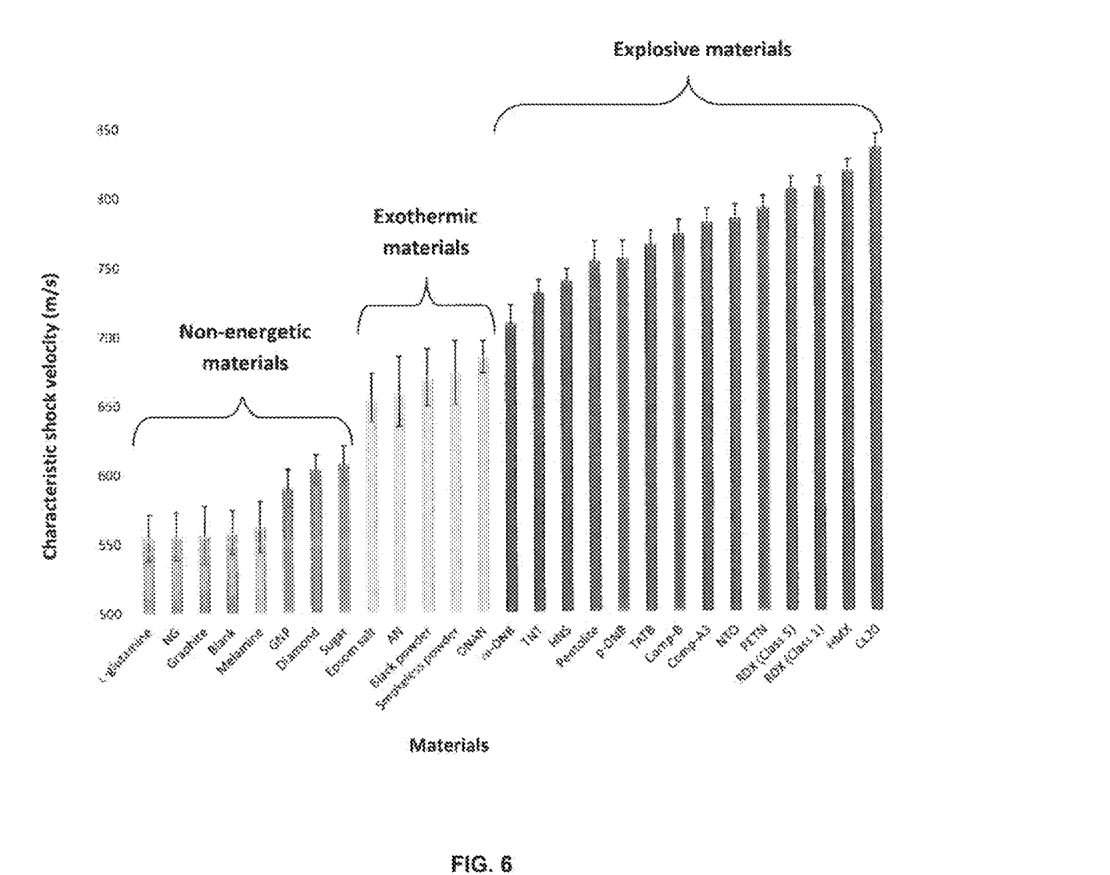
FIG. 6 is a chart illustrating different characteristic shock velocity values for various different energetic and non-energetic materials determined according to the innovative methodology.

FIG. 6 is a chart illustrating different characteristic shock velocity values for various different energetic and non-energetic materials determined according to the innovative methodology. The error bars represent 95% confidence intervals and reflect the shot-to-shot variations common with the laser ablation of powdered materials and the relatively limited number of laser shots (e.g., 5-8) recorded for each non-explosive sample (at least 40 shots were obtained for each explosive material). In general, non-energetic materials have lower characteristic shock velocities than energetic materials. CL-20, the most powerful conventional military explosive tested, produced the highest characteristic shock velocity.

For the described experimental conditions, non-energetic materials may be classified as having characteristic shock velocity values between roughly 550-600 m/s, exothermic materials (including non-explosive, energetic materials)

between 650-700 m/s, and explosive energetic materials above 750 m/s. Other threshold criteria may be used to classify materials in other implementations and embodiments. With this knowledge, the determined characteristic shock waves can clearly be used to discriminate between energetic and non-energetic materials as annotated on the plot in FIG. 6. This velocity value does not give much information about the properties of non-energetic materials other than to indicate whether it might make a good explosive. Nonetheless, this is still valuable information when investigating potential new explosive materials (e.g., materials that are theoretically predicted to be energetic may turn out not to be when they are synthesized).

As to the second purpose of step 18, the characteristic shock velocity of an energetic material sample determined according to the innovative methodology can be used to estimate its actual detonation performance.

Figure 7:
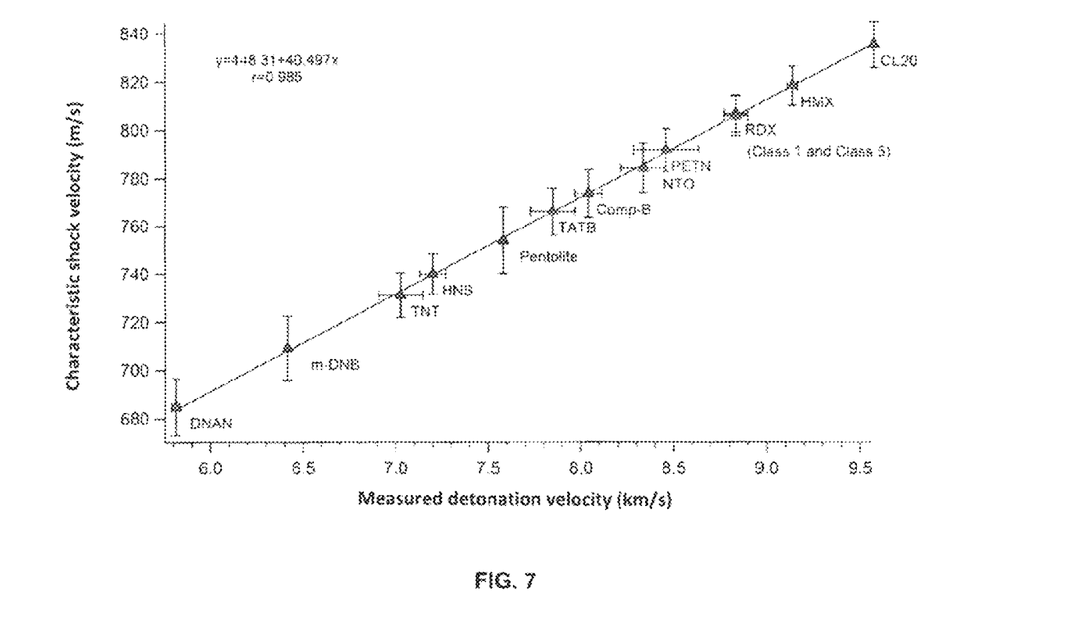
FIG. 7 shows a plot of characteristic shock velocity and corresponding measured detonation velocity values for various energetic materials as indicated by the data points on the plots.

FIG. 7 shows a plot of characteristic shock velocity and corresponding measured detonation velocity values for various energetic materials as indicated by the data points on the plots. The measured detonation velocities are reported literature values for these energetic materials. They were measured by detonating a large quantity of explosive on a testing range. These detonation test measurements are very expensive and dangerous to obtain without significant safety precautions. The characteristic shock velocity values were determined for these materials in step 16.

A best-fit line is also illustrated in the plot of FIG. 7. As should be quite apparent, there is a very strong relationship between these values. The linear correlation fit gives the relationship between the measured laser-induced shock velocity values and the measured detonation velocity values (reported in the literature). A separate calibration plot will likely needed for each system, as laser-induced shock velocities will depend on the specific type of laser used and the exact method of sample preparation (e.g., substrate type).

Once the calibration plot is generated, all that is needed to estimate the actual detonation performance of a material is to determine the characteristic shock velocity for the material. And then an estimation of the actual detonation performance of the sample material may be determined from its measured characteristic shock velocity. This is a great advantage over conventional large-scale detonation testing (using, for instance, hundreds to millions of grams of explosive). Not only is detonation testing very expensive and time consuming, measurements can be difficult because of the destructive nature of the tests. In many cases, scaling up production of new types of energetic materials for large-scale testing is prohibitively expensive without some prior assurance of performance gains over conventional explosives. By contrast, the novel methodology for estimating the detonation performance of an energetic material requires only small quantities of material. For instance, milligram quantities of energetic materials may suffice. As such they can safely be performed in a laboratory environment with minimal cost per test.

Additionally, other detonation performance parameters can be correlated to the characteristic shock velocity. For example, both the energy of detonation and the detonation pressure linearly correlate to the characteristic shock velocities of the explosive samples. It was found the heat of combustion for the explosive materials is not strongly correlated to the characteristic shock velocity.

The aforementioned digital processor or controller (or a separate one) may also be configured to: classify the sample material based on its characteristic shock velocity as being energetic or non-energetic; estimate the detonation performance for the sample material based on the determined characteristic shock velocity; and/or compare the characteristic shock velocity for the sample with theoretically predicted or empirical data from detonation of energetic material(s), in implementing the methodology.

This methodology also may be used as a potential screening tool for the development of new energetic materials and formulations prior to larger-scale detonative testing. This would be particularly useful in several situations: when candidate materials are only available in limited quantities; for energetic materials with a large critical diameter, where small-scale detonative testing is not possible; or for materials that require nonconventional means to induce detonation.

Potential sources of error in the laser-induced shock wave measurements can include differences in the absorption coefficients of the energetic materials, fluctuations in laser energy, jitter in the camera triggering, measurement of the shock positions, differences in the amount of material ablated from shot to shot, and unusually high luminosity in the first few camera frames that obscures the shock front. Ideally, a camera with a faster frame rate should be used to better measure the shock position at earlier times.

A still further advantage of the present invention is that the method of the present invention may be quickly and inexpensively performed in a laboratory. Furthermore, the method of the present invention may be safely conducted in a laboratory without any concern of accidental or unintended detonation of a larger sample of the energetic material.

Having described my invention, many modifications will become apparent thereto to those skilled in the art to which it pertains without deviation from the spirit of the invention as defined by the scope of the appended claims.

I claim:

1. A method for estimating detonation performance of a material comprising:
preparing a sample of the material;
lasing said sample with a laser beam having sufficient energy to induce a plasma from a portion of the sample and to produce a shock wave, without detonation of the sample;
measuring a velocity of the shock wave at different times; and
determining a characteristic shock velocity for the material based on the relationship between shock velocity and time, wherein the characteristic shock velocity represents the velocity of the shock wave at a point in time when a shock front expands freely without additional energy input from the plasma or subsequent chemical reactions.

2. The method as defined in claim 1, wherein the sample is about 10-20 mg.

3. The method as defined in claim 1, wherein the sample is applied to one side of a double-sided tape and another side of the double-sided tape is affixed to a glass slide.

4. The method as defined in claim 1, wherein said lasing comprises focusing the laser beam having an energy of about 900 millijoules/pulse, a wavelength of about 1064 nanometers, and a pulse duration of about 6 nanoseconds onto the sample.

5. The method as defined in claim 1, wherein a high-speed video camera is used to record the shock wave moment as a plurality images from a single laser shot.

6. The method as defined in claim 5, wherein velocity measurements of the shock wave are taken using successive images recorded by the video camera.

7. The method as defined in claim 5, wherein a linear scale with known dimensions is included as a part of the recorded shock wave.

8. The method as defined in claim 1, further comprising: applying a best fit function fitting the multiple velocity measurements as a function of time.

9. The method as defined in claim 8, wherein the best fit function is a 5th order polynomial.

10. The method as defined in claim 8, wherein the characteristic shock velocity is a y-intercept of the best fit function fitting the multiple velocity measurements as a function of time.

11. The method as defined in claim 1, further comprising: classifying the sample material based on the determined characteristic shock velocity as being energetic or non-energetic.

12. The method as defined in claim 1, further comprising: estimating the detonation performance for the sample material based on the determined characteristic shock velocity.

13. The method as defined in claim 12, wherein said estimating comprises comparing the characteristic shock velocity for the sample material with theoretically predicted or empirical data from detonation of energetic material(s).

14. An apparatus for estimating detonation performance of a material comprising:
    a stage for holding a sample of the material;
    a laser configured to output a laser beam having sufficient energy to ablate said sample and form a plasma from a portion of the sample and to produce a shock wave, without detonation of the sample;
    a high-speed camera configured to record movement of the shock wave in a plurality of sequential image frames; and
    a controller configured to:
    (i) measure a velocity of the shock wave at different times; and
    (ii) determine a characteristic shock velocity for the material based on the relationship between shock velocity and time, wherein the characteristic shock velocity represents the velocity of the shock wave at a point in time when a shock front expands freely without additional energy input from the plasma or subsequent chemical reactions.

15. The apparatus as defined in claim 14, wherein the laser is configured to focus the laser beam having an energy of about 900 millijoules/pulse, a wavelength of about 1064 nanometers, and a pulse duration of about 6 nanoseconds onto the sample.

16. The apparatus as defined in claim 14, further comprising: a schlieren imaging apparatus having:
    a pair of spaced-apart mirrors placed on opposing sides of the stage;
    an illumination source for focusing light onto a first of said pair of mirrors, through a sample laser-ablation area in a vicinity of the stage where the shock wave passes, and onto a second of said pair of mirrors; and
    an knife edge placed at a focal spot of the second of said pair of mirrors to limit light rays to the high-speed camera;
    wherein the high-speed camera photographs light and dark striations representing differences in a refractive index of air in the sample laser-ablation area.

17. The apparatus as defined in claim 14, wherein the controller is further configured to apply a best fit function fitting the multiple velocity measurements as a function of time.

18. The apparatus as defined in claim 17, wherein the controller is further configured to determine the characteristic shock velocity by finding a y-intercept of the best fit function fitting the multiple velocity measurements as a function of time.

19. The apparatus as defined in claim 14, wherein the controller is further configured to:
    (i) classify the sample material based on the determined characteristic shock velocity as being energetic or non-energetic;
    (ii) estimate the detonation performance for the sample material based on the determined characteristic shock velocity; and/or
    (iii) compare the characteristic shock velocity for the sample with theoretically predicted or empirical data from detonation of energetic material(s).

20. The apparatus as defined in claim 14, further comprising: an electronic database configured to store characteristic shock velocity values for materials.

* * * * *